United States Patent [19]
Biel

[11] Patent Number: 6,159,236
[45] Date of Patent: Dec. 12, 2000

[54] EXPANDABLE TREATMENT DEVICE FOR PHOTODYNAMIC THERAPY AND METHOD OF USING SAME

[75] Inventor: Merrill A. Biel, Minneapolis, Minn.

[73] Assignee: Advanced Photodynamic Technologies, Inc., Mendota Heights, Minn.

[21] Appl. No.: 09/239,353

[22] Filed: Jan. 28, 1999

[51] Int. Cl.[7] ............................. A61B 18/18; A61N 1/30
[52] U.S. Cl. ..................... 607/92; 606/2; 606/3; 606/14; 606/15; 606/16; 604/20; 604/21; 604/96
[58] Field of Search .................. 606/2, 3, 13–16, 606/21; 607/88, 89, 92; 604/20, 21, 96

[56] References Cited

U.S. PATENT DOCUMENTS

| 4,791,926 | 12/1988 | Fry | 128/303.1 |
|---|---|---|---|
| 4,822,335 | 4/1989 | Kawai | 604/20 |
| 5,169,395 | 12/1992 | Narciso, Jr. | 606/7 |
| 5,358,503 | 10/1994 | Bertwell et al. | 606/27 |
| 5,415,654 | 5/1995 | Daikuzono | 606/15 |
| 5,456,661 | 10/1995 | Narciso, Jr. | 604/20 |
| 5,611,793 | 3/1997 | Wilson et al. | 606/2 |
| 5,624,433 | 4/1997 | Radisch, Jr. | 606/7 |
| 5,741,246 | 4/1998 | Prescott | 606/7 |
| 5,797,868 | 8/1998 | Leone | 604/21 |
| 5,891,082 | 4/1999 | Leone et al. | 604/21 |

Primary Examiner—Linda C. M. Dvorak
Assistant Examiner—Jocelyn Ram
Attorney, Agent, or Firm—Larkin, Hoffman, Daly & Lindgren, Ltd.

[57] ABSTRACT

The invention relates to a medical device including a tube and expandable member and one or more light sources disposed in an elongated member disposed in the tube. The light sources emit energy for photodynamic therapy through a window to the treatment area. The treatment device may further include a heat and/or light dissipating layer, such as a layer of gold alloy paint, or other light blocking material.

20 Claims, 2 Drawing Sheets

EXPANDABLE TREATMENT DEVICE FOR PHOTODYNAMIC THERAPY AND METHOD OF USING SAME

BACKGROUND OF THE INVENTION

The invention relates to a medical device for photodynamic therapy (PDT). More specifically, the invention relates to an expandable member and light source for PDT treatment of a body lumen such as larynx or a body portion such as a check. The present invention advantageously uses light energy to treat or detect pathologies of living tissue, including cancer and microbiological pathogens. The present invention may be used in combination with photosensitizing agents.

U.S. Pat. No. 4,822,335, entitled, *Apparatus For Treatment Of Cancer With Photodiode,* purportedly discloses an apparatus for the treatment of a cancerous lesion part by irradiating a light energy from a light source to the cancerous lesion part having absorbed and accumulated in advance therein a photosensitive substance with an affinity for tumors. The light source comprises a first diode adapted to excite the photosensitive substance from the ground state to a singlet state of higher energy level and a second photodiode adapted to excite an energy level of the photosensitive substance which has transited from the singlet state to a triplet state to a still higher energy level.

U.S. Pat. No. 5,358,503, entitled, *Photo-Thermal Therapeutic Device and Method,* purportedly discloses an apparatus for simultaneous or selective treatment of an area of the skin and adjacent subcutaneous structure of a patient utilizing photo energy and therapeutic heat, which includes a plurality of juxtaposed diodes. Each diode has a longitudinal axis and is capable of projecting a non-coherent cone of light which overlaps the cone of light from each juxtaposed diode so that the light completely covers the treatment area. A pad or appliance holds the diodes in juxtaposed position with each other.

U.S. Pat. No. 5,611,793, entitled, *Laser Treatment,* purportedly disclose a method of disinfecting or sterilizing tissues of the oral cavity or a wound or lesion in the oral cavity. The method includes applying a photosensitizing compound to the tissue and irradiating with laser light at a wavelength absorbed by the photosensitizing compound.

U.S. Pat. No. 4,791,926, entitled, *Method of Controlling Laser Energy Removal of Plaque to Prevent Vessel Wall Damage,* purportedly discloses a method of controlling laser energy removal of plaque or other obstructions from the vessel of the cardiovascular system.

All documents cited herein, including the foregoing, are incorporated hereby by reference in their entireties for all purposes.

SUMMARY OF THE INVENTION

The invention relates to a PDT treatment device which is configured to deliver light energy to a treatment site from one or more light emitting members disposed in a lumen of the treatment device. The treatment device may include a flexible or rigid tube and an expandable member on the distal portion of the tube. The light emitting members operate at wavelengths ranging from about 450 nm to about 850 nm; a dosage rate ranging from about 0 to 150 mw/cm$^2$; and a light dose ranging from 0 to about 300 J/cm$^2$. The treatment device may have surface monitor capabilities which include isotropic or anisotropic light detectors or photodetectors. The light detectors may be used in combination with a controller to automatically monitor light dosage, light power and dosage rate. The treatment device may contain an integrated array of vertical cavity surface emitting lasers (VCSEL) as a light emitting source for PDT treatment. The treatment device is configured to direct energy for PDT treatment of, for example, a disease in the throat or cheek.

In sum, the invention relates to a medical device for photodynamic therapy including an elongated tube having a proximal end, a distal end and a lumen. An expandable member is disposed on a distal portion of the tube. The expandable member is adapted to expand and contract to one or more states via application of internal pressure from air or other fluid, or a gel or other viscous material. Associated with the elongated tube and expandable member is an elongated member having one or more light sources. The elongated member is disposed in at least a portion of the tube or expandable member. The elongated member may be slidably movable within the lumen of the elongated tube. The one or more light sources emit energy for photodynamic therapy. The energy for photodynamic therapy may pass through at least a portion of the medical device. The energy for photodynamic therapy may pass substantially unrestricted through at least a portion of the medical device. The one or more light sources may provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$. A portion of the expandable member may substantially restrict the energy for photodynamic therapy from exiting the medical device. The expandable member may have a cross-sectional shape that is triangular-like. The lumen may open at the distal end of the elongated tube. A heat dissipating layer may be disposed on a portion of the expandable member. A layer of gold or gold alloy or other light blocking material may be disposed on the expandable member for light control purposes. At least a portion of the elongated member may be made of a light diffusing material. A remote light source may be operatively coupled to the elongated member via at least one of a fiber optic element, a plurality of internal filaments, or one or more VCSELs. The medical device and expandable member may be made of a polymer. The expandable member may be inflated under pressure from a variety of fluids (air, saline, etc.), gels, or other viscous materials. A control device may be operatively coupled to the light source to provide at least one of a range of intensity or selective operation of the emitted energy. The tube and the expandable member may include a window for substantially unobstructed delivery of a light emitting source to a portion of a body.

The invention also relates to a medical device for photodynamic therapy including one or more light sources disposed in a balloon catheter. The balloon catheter has one or more windows for passage of light energy. The one or more light sources emit energy for photodynamic therapy through at least one window at a treatment site.

The invention also relates to a medical device for photodynamic therapy including a catheter having a balloon disposed thereon. The balloon is to be juxtaposed one or more body portions. One or more light sources are disposed within the balloon. The one or more light sources emit energy for photodynamic therapy. The one or more light sources provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$.

The invention also relates to a method of using a light emitting treatment device including identifying a treatment site in a body; disposing an expandable member at the treatment site; positioning the expandable member to direct the light source to emit energy at the treatment site; and activating the light source for a period of time to emit energy at the treatment site for photodynamic therapy. The one or more light sources are configured to provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$. The method may further include injecting a drug or dye at the treatment site.

The invention also relates to a light emitting treatment device including an expandable member configured to conform to one or more treatment surfaces. One or more light members are disposed in the expandable member. The expandable member and the one or more light sources form an assembly and the one or more light members are configured to emit energy from the assembly for photodynamic therapy of the one or more treatment surfaces. The expandable member may include one or more light detectors configured to provide monitoring of the treatment surface. The monitoring may include at least one of light wavelength (nm), light dosage (joules/cm$^2$), or light dosage rate (mw/cm$^2$).

The present invention may be used with inventions disclosed in the following U.S Patent Applications:

Method of Enhancing Photodynamic Therapy by Administering an Immunologic Adjuvant, Ser. No. 09/139,861, commonly assigned to the assignee of this application;

Dye Treatment Solution and Photodynamic Therapy and Method of Using Same, Ser. No. 09/139,866, commonly assigned to the assignee of this application;

Spatial Orientation Grid and Light Sources and Method of Using Same for Medical Diagnosis and Photodynamic Therapy, Ser. No. 09/139,862, commonly assigned to the assignee of this application;

Rectangular Laser Irradiation Field Producing Apparatus for Medical Treatment, Ser. No. 09/139,480, commonly assigned to the assignee of this application; and Methylene Blue and Toluidene Blue Mediated Fluorescence Diagnosis of Cancer, Ser. No. 09/139,481, commonly assigned to the assignee of this application.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

In accordance with this invention, a medical device 10 is used to treat a body lumen 11 or body portion with photodynamic therapy (PDT).

Figure 1:
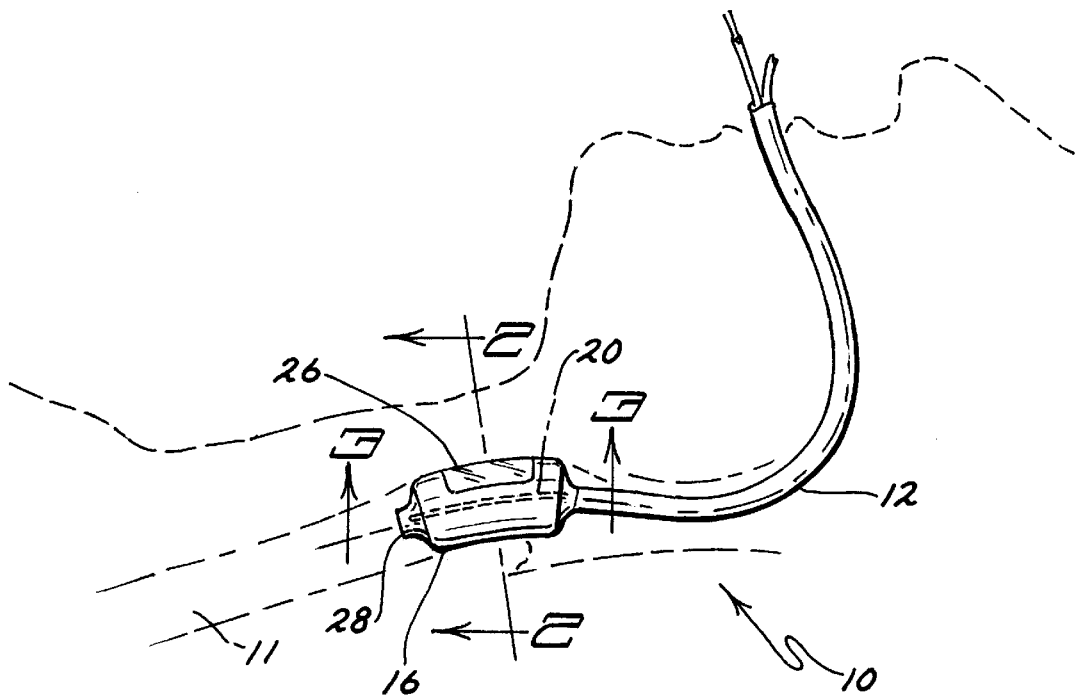
FIG. 1 is a plan view of a preferred embodiment of the expandable treatment device having PDT light-emitting capabilities disposed in a body lumen.

Reference is made to FIG. 1 which illustrates a medical device 10 including a tube 12, expandable member 16, and light source 20 for PDT. The medical device 10 is shown disposed in a body lumen 11, for example, at a larynx. The treatment device 10 is used to treat tissue with topical or surface exposure of PDT. The expandable member 16 is expanded, via an inflation lumen, by air or fluid including a light diffusing gel such as INTRALIPID (protein solution). The expandable member 16 may be sufficiently flexible to conform to a variety of body shapes or parts such as the throat, tongue, palate, or cheek, as well as complex or irregular body curvatures. In the illustrated embodiments of FIGS. 1–3, the expandable member 16 includes an air aperture 28 for ventilation purposes during the PDT procedure. Air aperture 28 in communication with an associated ventilation system (not shown) permits normal respiratory system function during the PDT procedure.

Figure 2:
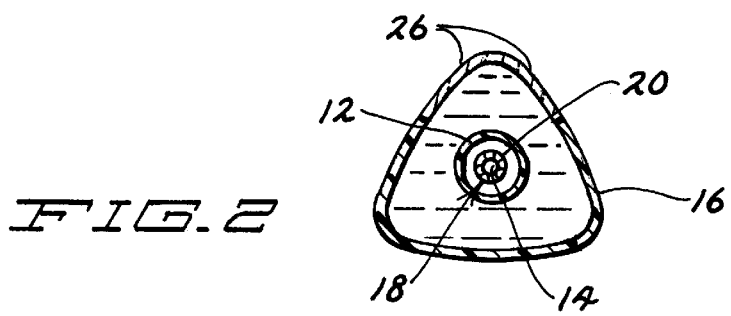
FIG. 2 is a cross-sectional view of the expandable treatment member of FIG. 1 taken along the line 2—2.
Figure 3:
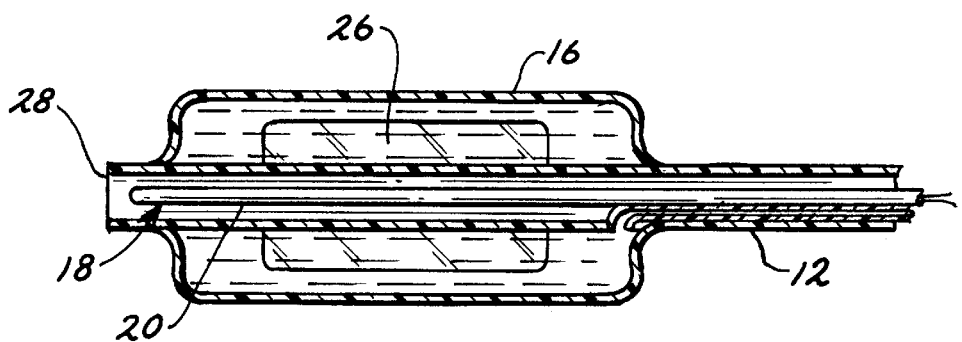
FIG. 3 is a cross-sectional view of the expandable treatment member of FIG. 1 taken along the line 3—3.

FIGS. 2 and 3 show a preferred embodiment of the expandable member 16 having a triangular profile. Other shapes of the expandable member 16 are envisioned including disk shapes, curvilinear shapes, rectangles, etc. The tube 12 and expandable member 16 are preferably made of one or more materials that are generally clear and provide a sufficient texture or internal turbidity for suitable light-diffusing characteristics. A window 26 may be disposed in a portion of the tube 12 and in the expandable member 16 to allow passage of the light energy from the light source 20 to a treatment site. A suitable material for the tube 12, expandable member 16, and window 26 is clear silicone or vinyl substances. A window 26 may be formed by disposing a layer of material, such as gold or light blocking paint, on one or more surfaces of the expandable member 16 or tube 12 to direct the PDT to a certain area of the body. The layer may be added and/or configured at the time of treatment depending on the treatment area desired.

The light source 20 may include one or more optical filaments 20 incorporated in the medical device 10. The optical filaments may be formed integral with or operatively connected to an optical fiber and coupled with a remote light source. The optical filaments may be disposed in a suitable array which uniformly and efficiently disperses the light energy throughout the operative area of the medical device 10. The light source 20 may be a serpentine optical filament, a fiber optic element, or a plurality of internally embedded filaments.

The light source 20 may also include a plurality of VCSELs or light emitting diodes (LEDs) coupled to an independent power supply such as battery or other power source using a wire or cable. The light source 20 may be disposed in an elongated member 18 such as in a lumen 14 in an array or pattern. The VCSELs may be disposed in close proximity to one another, or spaced apart to facilitate flexing of the tube 12. The VCSELs may be any size, shape, or wavelength suitable for a variety of treatment applications. The number of VCSELs may vary depending on the required light output (mw/cm$^2$). The VCSELs may be separated or spaced-apart from the tissue surface by a predetermined distance that is dependent the incident light energy necessary for treatment, beam divergence, and the thickness or opacity of the light-diffusing layer. The separation may be approximately 1–2 mm.

An array of laser diode elements may be used for a light emission and transmission system for PDT. A plurality of laser diode elements may be operatively coupled to a thermal sink for carrying excess heat. The light source 20 may be wired in series, parallel, or combinations of series and parallel using suitable patterns.

The medical device 10 may have one or more surface monitor members such as isotropic or anisotropic light detectors or photodetectors. The surface monitor members may be used in combination with a controller to automatically monitor and control characteristics such as light wavelength (nm), light dosage (joules/cm$^2$), and light dosage rate (mw/cm$^2$).

Figure 4:
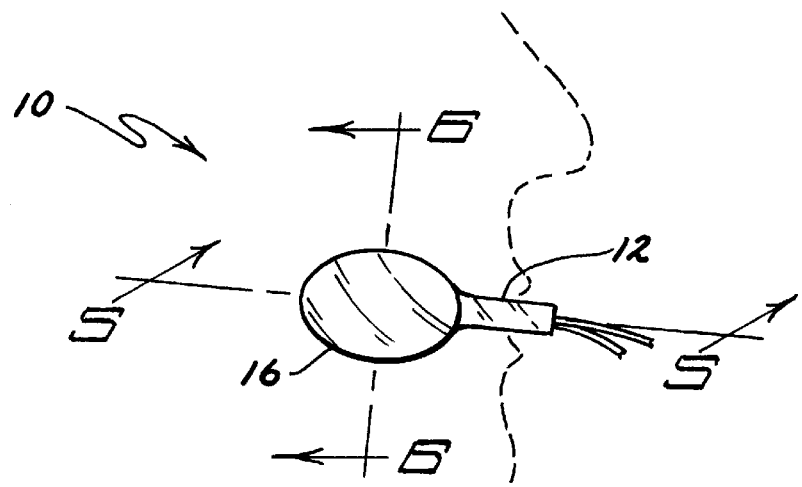
FIG. 4 is a plan view of another preferred embodiment of the expandable treatment device having PDT light-emitting capabilities disposed in a cheek area.
Figure 6:
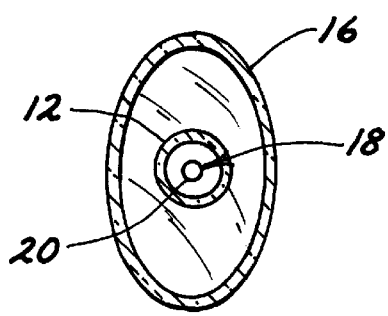
FIG. 6 is a cross-sectional view of the expandable treatment member of FIG. 4 taken along the line 6—6.
Figure 5:
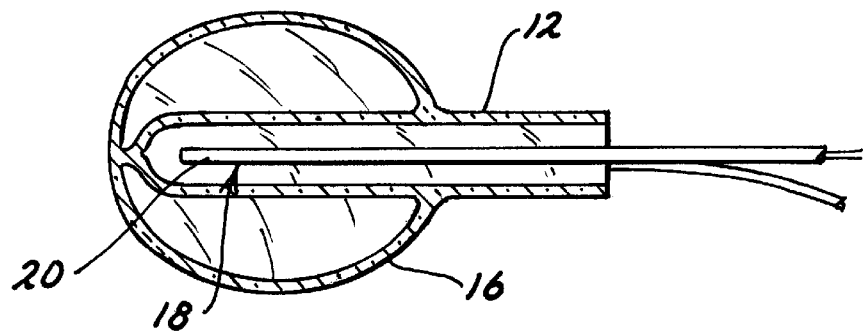
FIG. 5 is a cross-sectional view of the expandable treatment member of FIG. 4 taken along the line 5—5.

FIG. 4 illustrates another preferred embodiment of the expandable treatment device, in the form of a disk, having PDT light-emitting capabilities disposed in a cheek area. FIGS. 5 and 6 show cross-sectional views of the medical device 10 for use in a mouth, for example, on the inside of a cheek.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A medical device for photodynamic therapy comprising:
   a tube having a proximal end, a distal end and a lumen therein, an expandable member disposed on a distal portion of the tube, the expandable member configured to expand and contract to one or more states; and
   an elongated member providing one or more light sources, the elongated member disposed in at least a portion of the tube, the one or more light sources configured to emit energy for photodynamic therapy, and wherein the elongated member is slidably movable within the lumen of the elongated tube.

2. The medical device for photodynamic therapy of claim 1 wherein the energy for photodynamic therapy passes through at least a portion of the medical device.

3. The medical device for photodynamic therapy of claim 2 wherein the energy for photodynamic therapy passes substantially unrestricted through at least a portion of the medical device.

4. The medical device for photodynamic therapy of claim 1 wherein the one or more light sources provides light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$.

5. The medical device for photodynamic therapy of claim 1 wherein the expandable member has a cross-sectional shape that is triangular-like.

6. The medical device for photodynamic therapy of claim 1 further comprising a layer of gold or gold alloy disposed on the expandable member.

7. The medical device for photodynamic therapy of claim 1 wherein at least a portion of the elongated member is made of a light diffusing material.

8. The medical device for photodynamic therapy of claim 1 further comprising a remote light source operatively coupled to the elongated member via at least one of a fiber optic element, a plurality of internal filaments, or one or more VCSELs.

9. The medical device for photodynamic therapy of claim 1 wherein the elongated member is configured to treat disease in the throat or cheek.

10. The medical device for photodynamic therapy of claim 1 wherein the expandable member is made of a polymer.

11. The medical device for photodynamic therapy of claim 1 wherein the tube and the expandable member further including a window for substantially unobstructed delivery of a light emitting source to a portion of a body.

12. A medical device for photodynamic therapy comprising:
   a catheter having a balloon disposed thereon, said catheter providing a lumen therewithin for ventilation purposes, the balloon configured to be juxtaposed to one or more body portions; and
   one or more light sources in light communication with the balloon, the one or more light sources configured to emit energy from the balloon for photodynamic therapy;
   wherein the one or more light sources provide light wavelengths ranging from about 450 nm to about 850 nm; a light dosage rate ranging from about 0 to mw/cm$^2$ to about 150 mw/cm$^2$; and a light dose ranging from 0 J/cm$^2$ to about 300 J/cm$^2$.

13. A method of using a light emitting treatment device comprising the steps of:
   identifying a treatment site in a body;
   providing a tube having a proximal end, a distal end and a lumen therein, an expandable member being disposed proximate the distal end of the tube;
   providing an elongated member having one or more light sources, the elongated member being disposed in at least a portion of the tube;
   providing a control device coupled to the light source to provide at least one of a range of intensity or selective operation of an emitted light energy;
   disposing the expandable member at the treatment site;
   positioning the expandable member to direct the light source to emit energy at the treatment site, the one or more light sources configured to provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$; and
   activating the light source and the control device for a period of time to emit energy at the treatment site for photodynamic therapy.

14. A light emitting treatment device comprising:
   an expandable member configured to conform to one or more treatment surfaces;
   one or more light members in light communication with the expandable member; wherein the expandable member and the one or more light members form an assembly and the one or more light members are configured to emit energy from the assembly for photodynamic therapy of the one or more treatment surfaces; and
   one or more light detectors in light communication with the expandable member and configured to provide monitoring of the one or more treatment surfaces.

15. The light emitting treatment device of claim 14 wherein the monitoring includes at least one of light wavelength (nm), light dosage (joules/cm$^2$), or light dosage rate (mw/cm$^2$).

16. A medical device for photodynamic therapy comprising:
  a tube having a proximal end, a distal end and a lumen therein, an expandable member disposed on a distal portion of the tube, the expandable member configured to expand and contract to one or more states; and
  an elongated member providing one or more light sources, said elongated member being disposed in at least a portion of the tube, the one or more light sources configured to emit energy for photodynamic therapy; and
  a heat dissipating layer disposed on a portion of either the tube or the elongated member or both.

17. A medical device for photodynamic therapy comprising:
  a tube having a proximal end, a distal end and a lumen therein, an expandable member disposed on a distal portion of the tube, the expandable member configured to expand and contract to one or more states;
  one or more light sources disposed in at least a portion of the tube, the one or more light sources configured to emit energy for photodynamic therapy; and
  a control device operatively coupled to the light source to provide at least one of a range of intensity or selective operation of the emitted energy.

18. A light emitting treatment device comprising:
  an expandable member configured to conform to one or more treatment surfaces, a portion of the expandable member being configured to substantially restrict light energy for photodynamic therapy from exiting the treatment device; and
  one or more light members in light communication with the expandable member, wherein the expandable member and the one or more light members form an assembly and the one or more light members are configured to emit energy from the assembly for photodynamic therapy of the one or more treatment surfaces.

19. A method of using a light emitting treatment device comprising the steps of:
  identifying a treatment site in a body;
  disposing the expandable member at the treatment site;
  providing a light source in light communication with the expandable member;
  injecting a drug or dye at the treatment site;
  positioning the expandable member to direct the light source to emit energy at the treatment site, the one or more light sources configured to provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$; and
  activating the light source for a period of time to emit energy at the treatment site for photodynamic therapy.

20. A medical device for photodynamic therapy comprising:
  a catheter having a distal end adapted to be placed within a cavity of a body, said catheter providing a lumen for respiratory ventilation purposes of the body; and
  one or more light sources in light communication with the catheter, the one or more light sources configured to emit energy for photodynamic therapy;
  wherein the one or more light sources provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$.

* * * * *